United States Patent
Behnke, II

(10) Patent No.: US 9,861,425 B2
(45) Date of Patent: Jan. 9, 2018

(54) SYSTEM AND METHOD FOR USING RESONANCE PHASING FOR MEASURING IMPEDANCE

(71) Applicant: COVIDIEN LP, Mansfield, MA (US)

(72) Inventor: Robert J. Behnke, II, Erie, CO (US)

(73) Assignee: Covidien LP, Mansfield, MA (US)

( * ) Notice: Subject to any disclaimer, the term of this patent is extended or adjusted under 35 U.S.C. 154(b) by 623 days.

(21) Appl. No.: 13/971,553

(22) Filed: Aug. 20, 2013

(65) Prior Publication Data

US 2014/0094796 A1  Apr. 3, 2014

Related U.S. Application Data

(60) Provisional application No. 61/709,015, filed on Oct. 2, 2012.

(51) Int. Cl.
*A61B 18/12* (2006.01)
*A61B 18/00* (2006.01)
*A61B 18/16* (2006.01)

(52) U.S. Cl.
CPC ...... *A61B 18/1233* (2013.01); *A61B 2018/00851* (2013.01); *A61B 2018/00875* (2013.01); *A61B 2018/165* (2013.01)

(58) Field of Classification Search
CPC ......... A61B 18/04; A61B 18/08; A61B 18/10; A61B 18/12; A61B 18/1206;
(Continued)

(56) References Cited

U.S. PATENT DOCUMENTS

| 4,416,276 A | 11/1983 | Newton et al. |
| 4,416,277 A | 11/1983 | Newton et al. |

(Continued)

FOREIGN PATENT DOCUMENTS

| DE | 179607 | 3/1905 |
| DE | 1099658 | 2/1961 |

(Continued)

OTHER PUBLICATIONS

U.S. Appl. No. 10/406,690, filed Apr. 3, 2003, Robert J. Behnke, II.
(Continued)

*Primary Examiner* — Michael Peffley
*Assistant Examiner* — Khadijeh Vahdat

(57) ABSTRACT

A return electrode monitoring (REM) system for an electrosurgical system is disclosed. The REM system includes circuit components or circuitry for monitoring the magnitude of an interrogation or drive signal, and one or more electrode pads including one or more pairs of split electrode pads. The REM system, while sweeping an interrogation signal over or across a frequency range, monitors the magnitude of the interrogation signal. The REM system determines if there is a frequency shift in the interrogation signal. If there is a frequency shift, the REM system determines the frequency shift and uses it to calculate a reactance value of the impedance. The complex impedance can then be determined. The complex impedance, or at least the reactance value, can be used to determine the capacitive coupling between the patient and pad interface.

20 Claims, 5 Drawing Sheets

(58) Field of Classification Search
CPC . A61B 18/1233; A61B 18/1266; A61B 18/14; A61B 18/1442; A61B 18/1445; A61B 18/1447; A61B 18/1448; A61B 18/1449; A61B 2018/00851; A61B 2018/00875; A61B 2018/165
USPC .................................................. 606/33–41
See application file for complete search history.

(56) References Cited

U.S. PATENT DOCUMENTS

| | | | |
|---|---|---|---|
| 4,848,335 | A | 7/1989 | Manes |
| 5,766,165 | A | 6/1998 | Gentelia et al. |
| 6,074,386 | A * | 6/2000 | Goble ............... A61B 18/1206 606/34 |
| 6,258,085 | B1 | 7/2001 | Eggleston |
| 6,275,786 | B1 | 8/2001 | Daners |
| D574,323 | S | 8/2008 | Waaler |
| 7,637,907 | B2 | 12/2009 | Blaha |
| 7,927,329 | B2 | 4/2011 | McPherson |
| 8,080,007 | B2 | 12/2011 | Dunning et al. |
| 8,100,898 | B2 | 1/2012 | Gregg |
| 8,187,263 | B2 | 5/2012 | Behnke et al. |
| 8,216,222 | B2 | 7/2012 | McPherson |
| 8,231,614 | B2 | 7/2012 | Dunning et al. |
| 8,298,225 | B2 | 10/2012 | Gilbert |
| 8,382,749 | B2 | 2/2013 | Dunning et al. |
| 8,388,612 | B2 | 3/2013 | Dunning et al. |
| 8,430,873 | B2 | 4/2013 | Gregg |
| 8,523,853 | B2 | 9/2013 | Dunning |
| 2003/0028183 | A1* | 2/2003 | Sanchez ............... A61B 5/0422 606/34 |
| 2006/0224150 | A1 | 10/2006 | Arts et al. |
| 2008/0281311 | A1 | 11/2008 | Dunning et al. |
| 2009/0036884 | A1 | 2/2009 | Gregg et al. |
| 2009/0171341 | A1 | 7/2009 | Pope et al. |
| 2009/0198229 | A1 | 8/2009 | Dunning |
| 2009/0198230 | A1* | 8/2009 | Behnke ............... A61B 18/1233 606/35 |
| 2010/0241023 | A1 | 9/2010 | Gilbert |
| 2010/0331835 | A1 | 12/2010 | Shilev |
| 2012/0109121 | A1 | 5/2012 | Gregg |
| 2012/0232548 | A1 | 9/2012 | Behnke, II et al. |
| 2013/0158543 | A1 | 6/2013 | Dunning et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008058737 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| EP | 2 085 044 A1 | 8/2009 |
| EP | 2 103 269 A1 | 9/2009 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 63 005876 | 1/1988 |
| JP | 2002-065690 | 3/2002 |
| JP | 2005-185657 | 7/2005 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO06/050888 | 5/2006 |
| WO | WO08/053532 | 5/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/485,083, filed May 31, 2012, Robert J. Behnke, II.
U.S. Appl. No. 13/889,517, filed May 8, 2013, Behnke.
U.S. Appl. No. 13/898,632, filed May 21, 2013, Moul.
U.S. Appl. No. 13/902,011, filed May 24, 2013, Prakash.
U.S. Appl. No. 13/928,963, filed Jun. 27, 2013, Lopez.
U.S. Appl. No. 13/943,518, filed Jul. 16, 2013, Orszulak et al.
U.S. Appl. No. 13/971,553, filed Aug. 20, 2013, Behnke.
U.S. Appl. No. 13/971,596, filed Aug. 20, 2013, Collins.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

(56) References Cited

OTHER PUBLICATIONS

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and its Effect on Tissue Impedance" Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
Extended European Search Report dated Jan. 30, 2014 for EP 13 18 7079.

* cited by examiner

SYSTEM AND METHOD FOR USING RESONANCE PHASING FOR MEASURING IMPEDANCE

CROSS REFERENCE TO RELATED APPLICATION

The present application claims the benefit of and priority to U.S. Provisional Application Ser. No. 61/709,015, filed on Oct. 2, 2012, the entire contents of which are incorporated herein by reference.

BACKGROUND

Technical Field

The present disclosure relates to electrosurgical apparatuses, systems and methods. More particularly, the present disclosure is directed to electrosurgical systems configured to measure impedance using resonance phasing during electrosurgical procedures.

Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue. In monopolar electrosurgery, the active electrode is typically part of the surgical instrument held by the surgeon and applied to the tissue to be treated. A patient return electrode is placed remotely from the active electrode to carry the current back to the generator and safely disperse current applied by the active electrode.

The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and, in turn, increasing the heating at the tissue site.

To address this problem various return electrodes and hardware circuits, generically called Return Electrode Contact Quality Monitors (RECQMs), were developed. Such systems relied on measuring the external impedance at the return electrode to calculate a variety of tissue and/or electrode properties. These systems detected peeling by identifying changes in amplitude of the impedance of the return electrodes.

An electrosurgical generator typically uses an interrogation signal to continuously measure the external impedance, without activating the generator. This is depicted with respect to generator 100 shown in FIG. 1. The interrogation signal (Sense) monitors the impedance external to the generator 100 while the generator's main power (Gen) is disconnected from the output. The interrogation signal is utilized in various monitoring circuits, such as RECQMs, Return Electrode Monitoring (REM) and Auto Bipolar sensor (ABP), that continuously monitor external impedance while the generator is inactive.

A more detailed example of an impedance sensing circuit is the REM circuit shown in FIG. 2 which is used in various commercially available generators and designated by reference numeral 200. The REM circuit 200 is a resonance circuit consisting of capacitors and a transformer within a generator 205. The circuit 200 resonates around 80 KHz; the same frequency as the REM clock (REM CLK) generated by controller board 210 for driving impedance detection circuitry 220. The controller board 210 also drives amplifier 230. The REM circuit 200 drives the interrogation signal into a split pad (REM PAD) 240 that is attached to the patient. The impedance detection circuitry 220 filters and rectifies the interrogation signal. The interrogation signal represents the magnitude of impedance (|Z|) that is across the REM pad 240.

The REM pad 240, in conceptual terms, is a parallel plate capacitor, which means the impedance of the pad 240 has a resistive and reactive part to the impedance. The reactance is the capacitive coupling and the resistance is the dielectric losses between the pads. FIG. 3 graphically represents the relation between the magnitude |Z|, the real R, and reactance X part of the impedance. Just measuring the magnitude will not give enough information to determine how much coupling versus the losses there is between the patient and the pad 240.

An example of where this information would be useful: if a REM pad is folded upon itself and only a small section is touching the patient, the existing REM circuit could give a false green indication. By knowing the reactance and resistance in this case, the generator would see a very high capacitance versus the resistance and be able to determine a fault condition.

The REM circuit 200 has a single frequency that is used to monitor the magnitude of the resonance circuit (REM CLK in FIG. 2). Any reactance placed in line with the REM circuit will shift the resonance frequency causing the magnitude at the monitoring frequency to reduce. Since the REM circuit 200 is only monitoring at one frequency, this shift will move the actual magnitude of the signal and the REM circuit 200 is left measuring the tail end of the shifted signal. This is shown in FIG. 4, where $V_{r\_oc}$ is the open circuit voltage of the REM circuit 200 when no pad attached; $Y_{r\_load}$ is the actual voltage with a pad attached; and $Y_{r\_REM}$ is the voltage the REM circuit 200 measures.

If a user adds the correct amount of capacitance in series with the single pad return electrode, the resonance frequency of the REM circuit 200 will shift, such that the REM circuit 200 will measure a valid impedance and override the REM circuit 200, thus defeating any safety mitigation.

Additionally, any drift in the resonance of the REM circuit can be an issue. As components heat and age over time there is a possibility of the resonance shifting from its original frequency. To date, it is believed there is no reliable way of tracking this change and/or compensating for any change that may occur.

SUMMARY

The present disclosure relates to an electrosurgical system, and more particularly to a return electrode monitoring (REM) system for an electrosurgical system. The REM system has circuit components or circuitry for monitoring the magnitude of an interrogation or drive signal, and one or more electrode pads including one or more pairs of split electrode pads. At least one of the circuit components of the REM system sweeps over a frequency range for driving the interrogation signal or drive signal into the one or more pairs of split electrode pads that are attached to a patient. The REM system, while sweeping the interrogation signal over or across the frequency range, monitors the magnitude of the interrogation signal. By monitoring the magnitude of the interrogation signal over a frequency range, the REM system determines if there is a frequency shift in a feedback signal. The feedback signal is created by sweeping the interrogation signal over the frequency range. If there is a frequency shift in the feedback signal, the various circuit components, including, for example, a filter/diplexer, a sensor, an analog filter, and a digital signal processor (DSP) having an analog-to-digital converter (ADC), a digital filter, a digitally controlled oscillator (DCO), a time delay line module, and a communication module for communicating with a controller via an isolation barrier, determine the frequency shift and use it to calculate a reactance value of the impedance. By determining the reactance value due to monitoring the magnitude of the interrogation signal, the REM system is able to determine the complex impedance.

The complex impedance, or at least the reactance value, can then be used to determine the capacitive coupling between the patient and pad interface. By knowing the capacitance value, this gives the generator the ability to determine the pad size as a small shift in frequency is related to a small capacitance, such as a preemie pad. Conversely, if the frequency shift is large, the capacitance is large and there could be multiple pads on the patient. This allows the controller to recognize various pads without the use of expensive identification schemes. It also allows the REM or electrosurgical system to determine when a non-recommended pad has been connected by determining when the frequency shift parameters, such as magnitude and frequency, are outside of pre-determined specifications. Additionally, the complex impedance enables a user to regulate the energy delivered to tissue.

According to one aspect of the present disclosure a return electrode monitoring ("REM") system is disclosed. The REM system includes circuit components for monitoring the magnitude of an interrogation or drive signal, and one or more electrode pads including one or more pairs of split electrode pads. In particular, the return electrode monitoring system includes at least one return electrode pad including at least one pair of split electrode pads; and processing circuitry operatively coupled to the at least one pair of split electrode pads. The processing circuitry is also operatively coupled to a controller for receiving and sweeping a drive signal over a frequency range. The drive signal generates at least one feedback signal. Frequency shift information corresponding to the feedback signal is used by the processing circuitry for determining a reactance of a complex impedance across the at least one pair of split electrode pads.

The processing circuitry which includes a digital signal processor (DSP) is configured to measure a voltage of the feedback signal. The processing circuitry is also configured to increase, decrease or keep constant a frequency of the drive signal in accordance with magnitude information corresponding to the feedback signal. The processing circuitry includes an oscillator configured to increase, decrease or keep constant a frequency of the drive signal in accordance with magnitude information corresponding to the feedback signal. The processing circuitry also includes a communication module for receiving a frequency signal and a magnitude signal corresponding to the feedback signal.

The controller is configured to determine at least one characteristic of the at least one pair of split electrode pads as a function of a change in amplitude of the voltage of the feedback signal. The change in amplitude is a measurement of the real part of the complex impedance. The controller is also configured to determine the complex impedance across the at least one pair of split electrode pads as a function of at least the reactance.

A method for monitoring a return electrode is also disclosed by the present disclosure. The method includes the steps of sweeping a drive signal over a frequency range of a return electrode monitoring system including at least one return electrode pad having at least one pair of split electrode pads; obtaining frequency shift information corresponding to a feedback signal which is generated in response to the drive signal; and determining a reactance of a complex impedance across the at least one pair of split electrode pads of the return electrode monitoring system using the frequency shift information.

The method further includes the step of measuring a voltage of the feedback signal. The method further comprises the step of increasing, decreasing or keeping constant a frequency of the drive signal in accordance with magnitude information corresponding to the feedback signal. The method also includes the step of determining at least one characteristic of the at least one pair of split electrode pads as a function of a change in amplitude of the voltage of the feedback signal. The change in amplitude is a measurement of the real part of the complex impedance. The method also includes the step of determining the complex impedance across the at least one pair of split electrode pads as a function of at least the reactance.

According to another aspect of the present disclosure an electrosurgical system is provided. The electrosurgical system includes a return electrode monitoring (REM) system and a controller. The REM system includes at least one return electrode pad including at least one pair of split electrode pads; and processing circuitry operatively coupled to the at least one pair of split electrode pads. The controller is operatively coupled to the processing circuitry and configured to generate a drive signal. The processing circuitry receives and sweeps the drive signal over a frequency range to create a feedback signal. Frequency shift information corresponding to the feedback signal is used by the processing circuitry for determining a reactance of a complex impedance across the at least one pair of split electrode pads.

The processing circuitry comprises a digital signal processor (DSP). The processing circuitry is configured to measure a voltage of the feedback signal. The processing circuitry is also configured to increase, decrease or keep constant a frequency of the drive signal in accordance with magnitude information corresponding to the feedback signal. The processing circuitry includes a communication module for receiving a frequency signal and a magnitude signal corresponding to the feedback signal.

The controller is configured to determine at least one characteristic of the at least one pair of split electrode pads as a function of a change in amplitude of the voltage of the feedback signal. The change in amplitude is a measurement of the real part of the complex impedance. The controller is also configured to determine the complex impedance across the at least one pair of split electrode pads as a function of at least the reactance.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A return electrode monitoring ("REM") system in an electrosurgical generator monitors the contact area between the patient and one or more return electrode pads. The circuitry prevents tissue issues caused by return pad due to poor pad contact. The REM system forms a resonant system with the split electrode pads of the return electrode pads which are designed to resonate at a specific interrogation frequency. The REM system detects a signal in response to a supplied drive signal at a predetermined clock frequency (e.g., from a controller).

The REM system thereafter produces a voltage indicative of the amplitude (e.g., magnitude) of the waveform indicative of the resonations. As the impedance between the split pads changes, the resonance of the REM system changes as well, this causes the amplitude to change. Thus, by monitoring the changes in the amplitude, the REM system determines the magnitude of the impedance between the split pads which is indicative of adherence of the return electrode pad to the patient.

The drive signal may be a square wave, a sine wave, an impulse or step signal. If the drive signal is either an impulse or a step signal, the frequency response can be determined by using conventional mathematical calculations, as well as using any type of waveform processing such as fast Fourier transform, any combination thereof, and the like.

The present disclosure provides for an REM system which determines shift in amplitude and frequency, and using these shifts determines the complex impedance, i.e., determines both the real and imaginary characteristics of the complex impedance. This is due to the fact that the shift in voltage amplitude is indicative of a shift in the real part of the impedance and a shift in frequency is indicative of a shift in the imaginary or reactance.

The imaginary part of the complex impedance or reactance provides a more detailed measurement of the adherence of the return electrode pad to the patient. More specifically, as the return electrode pad is placed on the patient, the reactance thereof (e.g., capacitance) changes the resonance frequency of the REM system. Thus, any detected changes to the reactance directly relate to the overall adherence factor of the return electrode pad.

One of the advantages of the REM system according to the present disclosure is that it only measures the magnitude of the voltage across frequency; there is no phase information to deal with.

Figure 1:
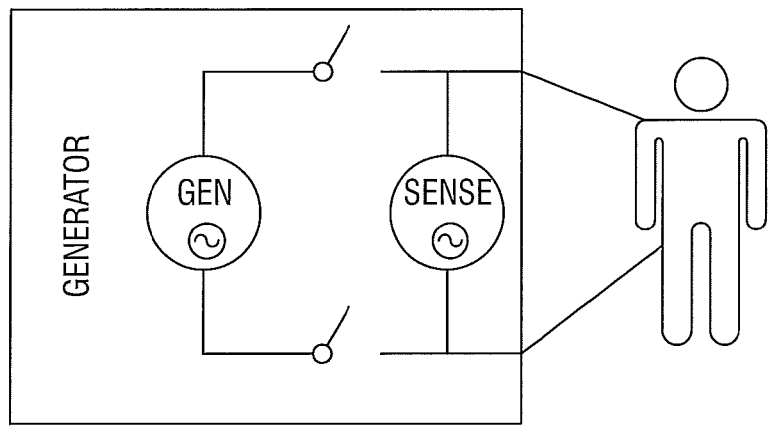
FIG. 1 is a prior art depiction of an electrosurgical generator for monitoring impedance.
Figure 2:
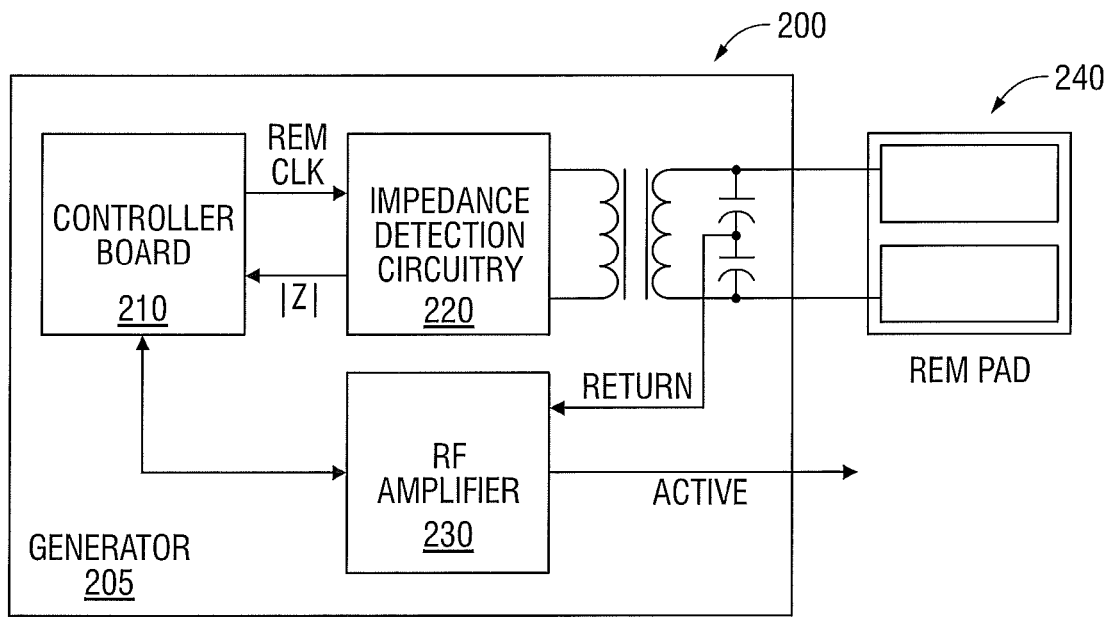
FIG. 2 is a prior art schematic block diagram of an electrosurgical generator.
Figure 3:
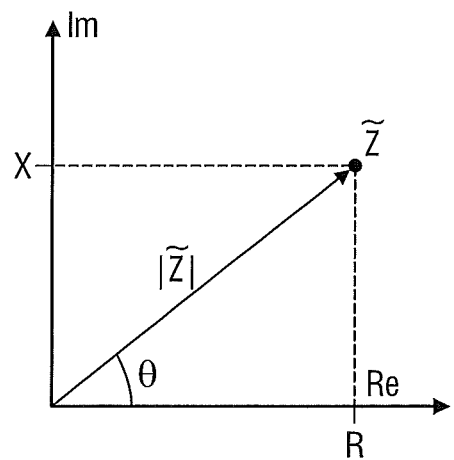
FIG. 3 is a graphical representation showing a return electrode monitoring (REM) pad acting like a parallel plate capacitor.
Figure 4:
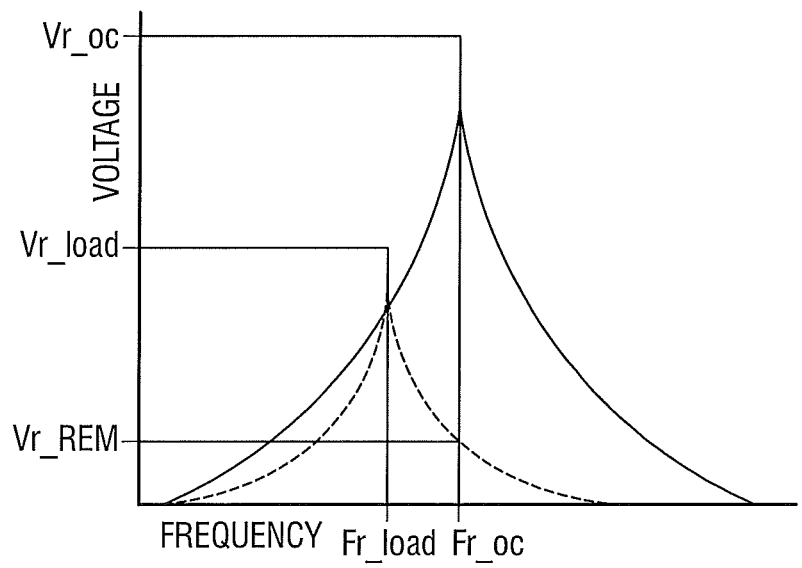
FIG. 4 is a graphical representation of the operation of a prior art REM circuit.
Figure 5:
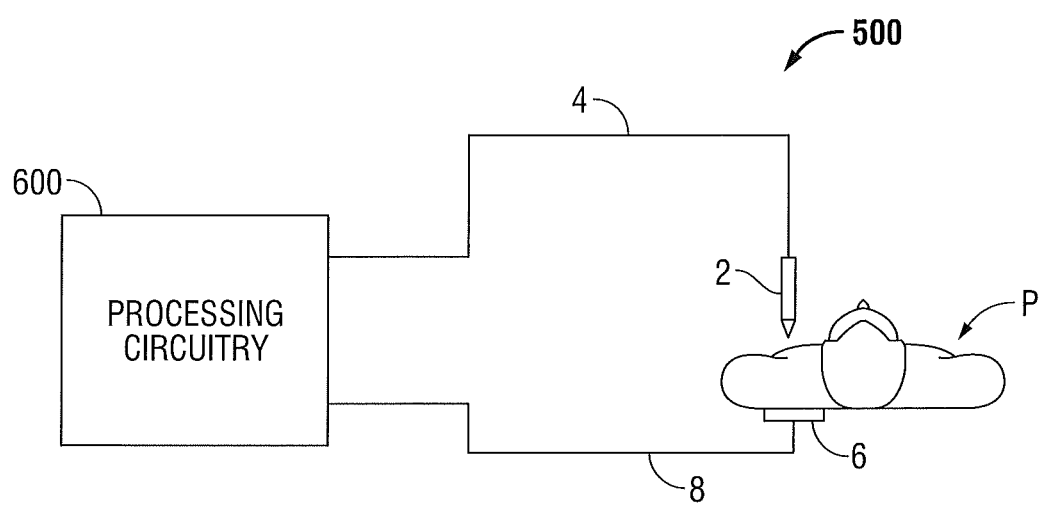
FIG. 5 is a schematic illustration of an electrosurgical system according to the present disclosure.

FIG. 5 is a schematic illustration of an electrosurgical return electrode monitoring (REM) system according to the present disclosure and designated generally by reference numeral 500. The REM system 500 includes an electrosurgical instrument 2 having one or more electrodes for treating tissue of a patient P. The instrument 2 is a monopolar instrument including one or more active electrodes (e.g., electrosurgical cutting probe, ablation electrode(s), etc.). Electrosurgical RF energy is supplied to the instrument 2 by processing circuitry 600 via an electrosurgical cable 4. The processing circuitry 600 is connected to a controller or generator 602 (see FIG. 6) for receiving and supplying electrosurgical RF energy to instrument 2. The instrument 2 is connected to an active output terminal, allowing the instrument 2 to coagulate, ablate and/or otherwise treat tissue. The energy is returned to the processing circuitry 600 through at least one return electrode pad 6 via a return cable 8. The system 500 may include a plurality of return electrodes pads 6 that are arranged to minimize the chances of tissue damage by maximizing the overall contact area with the patient P. In addition, the processing circuitry 600 and the return electrode pad 6 including at least one pair of split electrode pads may be configured for monitoring so-called "tissue-to-patient" contact to insure that sufficient contact exists therebetween to further minimize chances of tissue damage.

Figure 6:
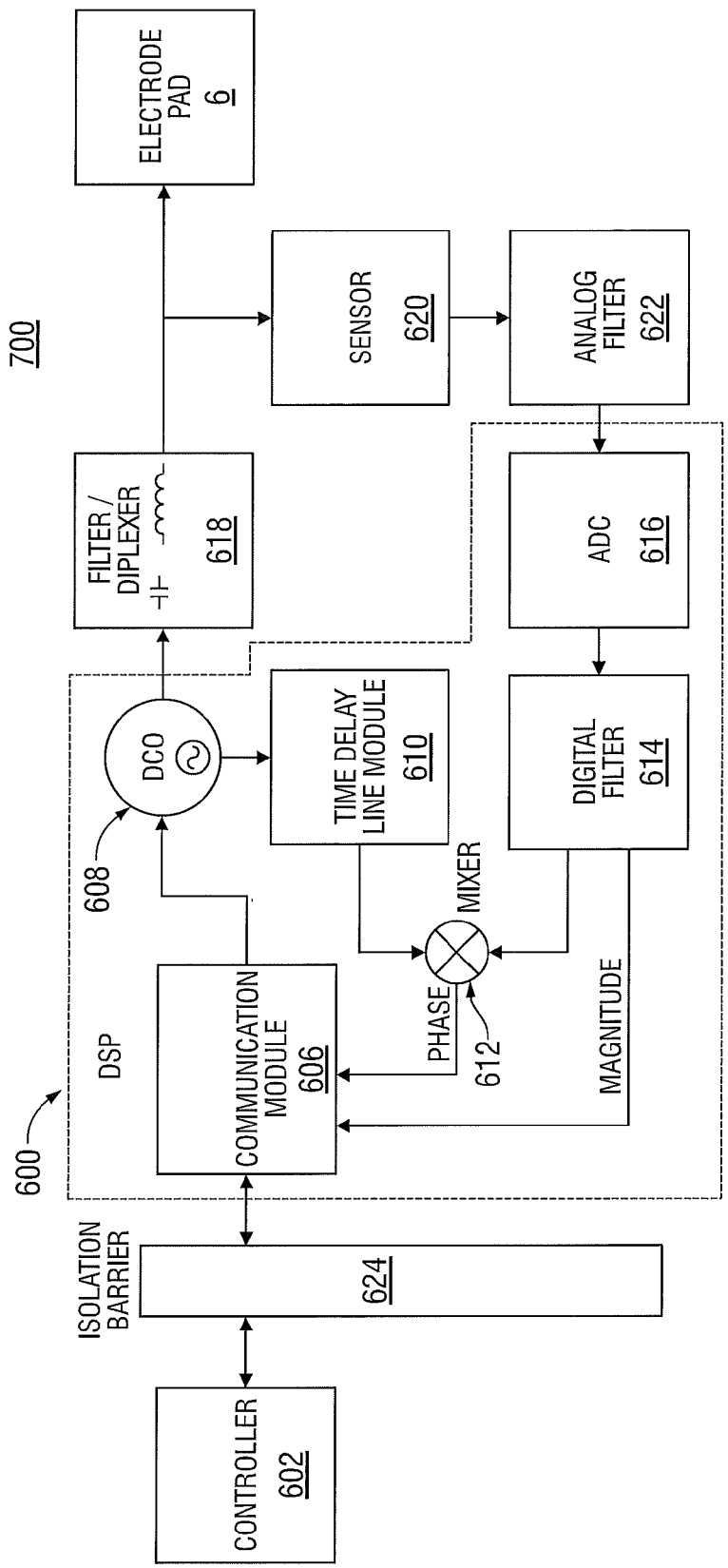
FIG. 6 is a schematic block diagram of a generator according to one embodiment of the present disclosure.

FIG. 6 is a schematic block diagram of an electrosurgical system 700 having processing circuitry 600, a controller 602, and one or more return electrode pads 6 including one or more pairs of split electrode pads according to one embodiment of the present disclosure. The circuit components of the processing circuitry 600 shown by FIG. 6 can be integrated with one or more additional circuit components. The arrangement of the circuit components may also be different from the arrangement shown by FIG. 6.

In essence, the schematic block diagram of the processing circuitry 600 shown by FIG. 6 is an exemplary embodiment according to the present disclosure. The various functions, such as the generation of the interrogation signal and the sensing of the frequency shift, are performed on the patient side. However, the various components described herein can be arranged such that all or several of the various functions described herein can be performed on the controller or generator side.

With continued reference to the circuit arrangement shown by FIG. 6, the processing circuitry is designated generally by reference numeral 600 and it includes several components arranged to function with at least one pair of split electrode pads of one or more return electrode pads 6 as a return electrode monitoring (REM) system 500. The controller 602 has communication capabilities for communicating across an isolation barrier 624 with a digital signal processor (DSP) 604. The DSP 604 according to the embodiment shown by FIG. 6 includes the following circuit components or modules whose main functions are described in detail below: communication module 606, digitally controlled oscillator (DCO) 608, time delay line module 610, a mixer 612, a digital filter 614 and an analog-to-digital converter (ADC) 616. The DSP 604 can include other types of processing circuitry, such as one or more application specific integrated circuits (ASICs).

The controller 602 includes input controls (e.g., buttons, activators, switches, touch screen, etc.) for controlling the controller 602 and its various functions. In addition, the controller 602 may include one or more display screens, including one or more touch screen displays, for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, cauterizing, intensity setting, etc.). The instrument 2 may also include a plurality of input controls that may be redundant with certain input controls of the controller 602. Placing the input controls at the instrument 2 allows for easier and faster modification of RF energy parameters during the surgical procedure without requiring interaction with the controller 602.

During operation of the processing circuitry 600, the DCO 608 controls the frequency of the interrogation signal. The interrogation signal is driven into the patient and then to the return electrode pad 6 having one or more pairs of split electrode pads via a filter/diplexer 618. The function of the filter/diplexer 618 is to inject the interrogation signal into the patient while blocking the high voltage signal of the controller 602, operating around 470 KHz. This can be accomplished with a high Q network consisting of a series inductor and capacitor that will resonate at 80 KHz. This will give low impedance at 80 KHz and high impedance at 470 KHz. The frequency of the interrogation signal is around 80 KHz.

One or more sensors 620 receive the voltage feedback which can be coupled off before, during, or after the filter/diplexer 618. In one embodiment of operating the controller 602, the voltage is measured before the filter/diplexer 618 using the blocking properties of the filter/diplexer 618 to reduce the signal-to-noise ratio on the feedback line.

The analog filter 622 is used to further reduce the noise from the controller 602. The analog filter 622 can also be used to condition the feedback signal for the ADC 616. The ADC 616 is used to real time digitize the feedback signal, for both frequency shift and voltage amplitude analysis by the DSP 604. The digital filter 614 may be needed if better signal-to-noise ratio is required for signal analysis by the DSP 604.

The communication module 606 is the control center of the DSP 604. It includes but is not limited to a memory storage and a microprocessor for executing software for performing the various functions of the DSP 604, including but not limited to, receiving the phase signal from the mixer 612, receiving the magnitude signal from the digital filter 614, generating a clock signal for transmission to the DCO 608, calculating the phase of the feedback signal, determining whether there was a shift in the phase of the feedback signal (i.e., frequency shift, such as, for example, frequency shift between the initial circuit response compared to the loaded circuit response) and accordingly determining whether to adjust the frequency of the DCO 608, and communicating with the DCO 608 for adjusting the frequency thereof.

The circuitry 600, instead of doing a constant frequency sweep of the interrogation signal, adjusts the frequency of the interrogation signal up or down (i.e., increase or decrease) depending on the voltage amplitude of the feedback signal (i.e., magnitude information of the feedback signal). Starting at the initial resonance frequency, if the interrogation signal is increased and the voltage amplitude drops, then the interrogation signal would be decreased. If the amplitude voltage has a maximum below the initial resonance, then the interrogation signal can be set to the new frequency. This process of checking for the amplitude maximum can occur a few times a second to ensure proper monitoring of the patient contact.

The initial frequency response of the processing circuitry 600 is determined by measuring the maximum voltage (i.e., magnitude) of the feedback signal with nothing connected or attached to the processing circuitry 600. The frequency response can also be rechecked over time by placing a switch in series with the REM transformer and REM pad, and opening the switch when necessary. The determined frequency and magnitude data can be stored in a memory device.

The communication module 606 also communicates with the controller 602 across the isolation barrier 624.

The controller 602 receives information from the DSP 604 during operation and monitors various parameters to determine, for example, whether a non-recommended REM pad is being used, whether the REM system 500 is operating within a safe operating protocol, whether the electrosurgical system 700 is malfunctioning to perform a shut down, etc.

Figure 7:
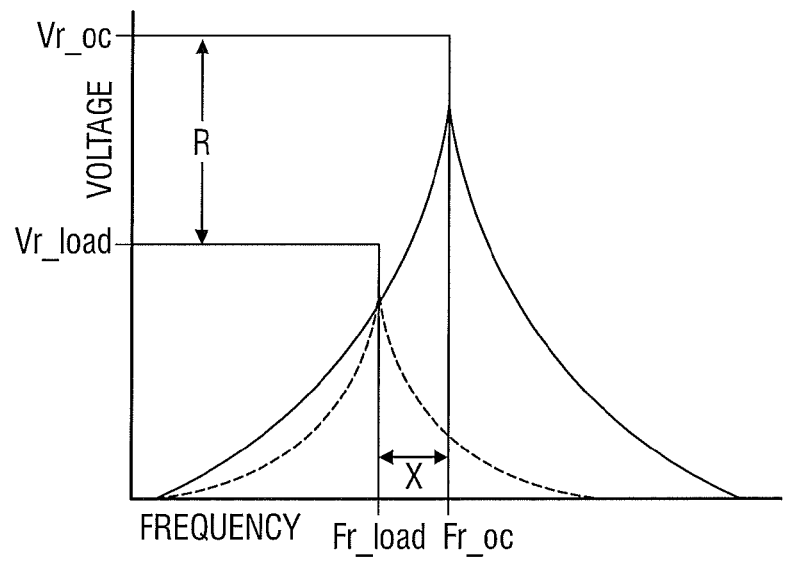
FIG. 7 is a graphical representation of the operation of the REM system according to the present disclosure.

By knowing the frequency shift of the feedback signal (X in FIG. 7), the reactance value of the impedance can be calculated by the communication module 606 or any other computing device of system 700, such as the controller 602. This is because a shift in frequency is indicative of a shift in reactance. By determining the reactance value due to monitoring the interrogation signal, the REM system is then able to determine a complex impedance.

The complex impedance, or at least the reactance value, can then be used to determine the capacitive coupling between the patient and pad interface. By knowing the capacitance value, this gives the controller 602 the ability to determine the pad size as a small shift in frequency is related to a small capacitance, such as a preemie pad.

Conversely, if the frequency shift is large, the capacitance is large and there could be multiple pads on the patient. This allows the generator to recognize various pads without the use of expensive identification schemes. It also allows the system to determine when a non-recommended pad has been connected to the system or some other non-recommended procedure has been performed by determining when the frequency shift parameters, such as magnitude and frequency, are outside of pre-determined specifications as further explained below with respect to a shift in magnitude.

In one embodiment, the communication module 606 supplies the impedance measurement to the controller 602 which determines whether the impedance is within a pre-determined range. If the impedance is out of range, which denotes excessive peeling of the return electrode pad 6, the controller 602 issues an alarm and/or adjusts the output of the RF energy (e.g., terminates RF energy supply).

The complex impedance also enables a user to regulate the energy delivered to tissue. By knowing the magnitude and frequency shift, algorithms can be developed to determine the amount of energy that can pass through a REM pad without causing excessive heating. If the power setting is too high for too long of a period, the controller or generator 602 could intervene and reduce the power to a safe level. The communication module 606 can be programmed for communicating the calculated reactance value and other information across the isolation barrier 624 to the controller 602.

Figure 8:
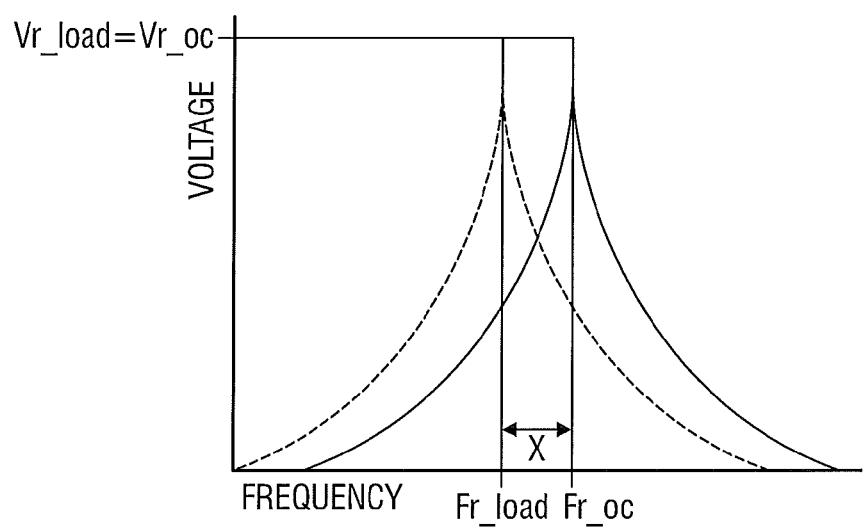
FIG. 8 is a graphical representation of the operation of the REM system according to the present disclosure showing detection of a non-recommended REM pad to the REM system.

The shift in magnitude (R in FIG. 7) determines the losses between the pad and the patient. If a user added capacitance to a return pad, to shift the frequency as shown in FIG. 8, the system 700, e.g., the controller 602, would detect a fake REM pad. This is because the R value is very small or close to zero as $V_{r\_oc} = V_{r\_load}$.

The system of the present disclosure can also be provided with a plurality of sensors along the shaft of an electro surgical probe to determine the impedance change of the tissue during ablation. The sensors could provide feedback information to inform the generator 600 when an ablation procedure has been completed. The system of the present disclosure can also be used in conjunction with a prior art REM circuit, such as the REM circuit 200, for verifying the impedance calculation of the prior art REM circuit.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A return electrode monitoring system, comprising:
at least one return electrode pad including at least one pair of split electrode pads; and
a processing circuitry operatively coupled to the at least one pair of split electrode pads and to a controller for receiving and sweeping a drive signal over a frequency range, the drive signal generating at least one feedback signal, wherein a frequency shift information corresponding to the at least one feedback signal is used by the processing circuitry for determining a reactance of a complex impedance across the at least one pair of split electrode pads, and wherein the frequency shift information is determined based on a magnitude information corresponding to the at least one feedback signal without using any phase information.

2. The return electrode monitoring system according to claim 1, wherein the frequency shift information is determined based on a magnitude maximum corresponding to the at least one feedback signal, the magnitude maximum occurring at a frequency below an initial resonance frequency.

3. The return electrode monitoring system according to claim 1, wherein the processing circuitry is configured to measure a voltage of the at least one feedback signal.

4. The return electrode monitoring system according to claim 3, wherein the controller is configured to determine at least one characteristic of the at least one pair of split electrode pads as a function of a change in amplitude of the voltage of the at least one feedback signal.

5. The return electrode monitoring system according to claim 1, wherein the processing circuitry is configured to increase, decrease or keep constant a frequency of the drive signal in accordance with the magnitude information corresponding to the at least one feedback signal.

6. The return electrode monitoring system according to claim 5, wherein the processing circuitry includes an oscillator configured to increase, decrease or keep constant a frequency of the drive signal in accordance with the magnitude information corresponding to the at least one feedback signal.

7. The return electrode monitoring system according to claim 1, wherein the processing circuitry includes a communication module for receiving a frequency signal and a magnitude signal corresponding to the at least one feedback signal.

8. The return electrode monitoring system according to claim 1, wherein the controller is configured to determine the complex impedance across the at least one pair of split electrode pads as a function of at least the reactance.

9. A method for monitoring a return electrode comprising the steps of:
sweeping a drive signal over a frequency range of a return electrode monitoring system including at least one return electrode pad having at least one pair of split electrode pads;
obtaining a frequency shift information corresponding to a feedback signal which is generated in response to the drive signal, wherein the frequency shift information is determined based on a magnitude information corresponding to the feedback signal without using any phase information; and
determining a reactance of a complex impedance across the at least one pair of split electrode pads of the return electrode monitoring system using the frequency shift information.

10. The method for monitoring a return electrode according to claim 9, further comprising a step of measuring a voltage of the feedback signal.

11. The method for monitoring a return electrode according to claim 10, further comprising a step of determining at least one characteristic of the at least one pair of split electrode pads as a function of a change in amplitude of the voltage of the feedback signal.

12. The method for monitoring a return electrode according to claim 9, further comprising a step of increasing, decreasing or keeping constant a frequency of the drive signal in accordance with the magnitude information corresponding to the feedback signal.

13. The method for monitoring a return electrode according to claim 9, further comprising a step of determining the complex impedance across the at least one pair of split electrode pads as a function of at least the reactance.

14. An electrosurgical system, comprising:
a return electrode monitoring system including:
at least one return electrode pad including at least one pair of split electrode pads;
a processing circuitry operatively coupled to the at least one pair of split electrode pads; and
a controller operatively coupled to the processing circuitry and configured to generate a drive signal, wherein the processing circuitry receives and sweeps the drive signal over a frequency range to create a feedback signal, wherein a frequency shift information corresponding to the feedback signal is used by the processing circuitry for determining a reactance of a complex impedance across the at least one pair of split electrode pads, wherein the frequency shift information is determined based on a magnitude information corresponding to the feedback signal without using any phase information.

15. The electrosurgical system according to claim 14, wherein the frequency shift information is determined based on a magnitude maximum corresponding to the feedback signal, the magnitude maximum occurring at a frequency below an initial resonance frequency.

16. The electrosurgical system according to claim 14, wherein the processing circuitry is configured to measure a voltage of the feedback signal.

17. The electrosurgical system according to claim 14, wherein the processing circuitry is configured to increase, decrease or keep constant a frequency of the drive signal in accordance with the magnitude information corresponding to the feedback signal.

18. The electrosurgical system according to claim 14, wherein the processing circuitry includes a communication module for receiving a frequency signal and a magnitude signal corresponding to the feedback signal.

19. The electrosurgical system according to claim 14, wherein the controller is configured to determine at least one characteristic of the at least one pair of split electrode pads as a function of a change in an amplitude of the voltage of the feedback signal.

20. The electrosurgical system according to claim 14, wherein the controller is configured to determine the complex impedance across the at least one pair of split electrode pads as a function of at least the reactance.

* * * * *